United States Patent
Abraham-Fuchs et al.

(10) Patent No.: US 8,182,499 B2
(45) Date of Patent: May 22, 2012

(54) DEVICE FOR REPEATED SEMI-INVASIVE ABRASION OF LESIONS ON THE WALLS OF HOLLOW ORGANS

(75) Inventors: Klaus Abraham-Fuchs, Erlangen (DE); Friedrich Fuchs, Roettenbach (DE); Rainer Kuth, Herzogenaurach (DE); Johannes Reinschke, Nuremberg (DE); Guenter Ries, Erlangen (DE); Rudolf Roeckelein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 805 days.

(21) Appl. No.: 11/064,838

(22) Filed: Feb. 25, 2005

(65) Prior Publication Data

US 2005/0209682 A1    Sep. 22, 2005

(30) Foreign Application Priority Data

Feb. 26, 2004  (DE) .......................... 10 2004 009 318

(51) Int. Cl.
*A61B 17/22* (2006.01)
(52) U.S. Cl. ....................................... 606/159
(58) Field of Classification Search .................. 606/159; 604/529; 600/424; 623/1.18, 1.42, 1.16
See application file for complete search history.

(56) References Cited

U.S. PATENT DOCUMENTS

| | | | | |
|---|---|---|---|---|
| 3,358,676 | A * | 12/1967 | Frei et al. | 600/12 |
| 5,681,260 | A * | 10/1997 | Ueda et al. | 600/114 |
| 6,036,708 | A * | 3/2000 | Sciver | 606/159 |
| 6,306,166 | B1 * | 10/2001 | Barry et al. | 623/1.46 |
| 6,325,823 | B1 * | 12/2001 | Horzewski et al. | 623/1.16 |
| 2003/0060702 | A1 | 3/2003 | Kuth et al. | |

FOREIGN PATENT DOCUMENTS

| | | |
|---|---|---|
| DE | 101 42 253 C1 | 4/2003 |
| DE | 10142253 C1 | 4/2003 |
| WO | WO 02/36047 A1 | 5/2002 |

\* cited by examiner

*Primary Examiner* — Ryan Severson
(74) *Attorney, Agent, or Firm* — Harness, Dickey & Pierce, P.L.C.

(57) ABSTRACT

A device is for repeated semi-invasive abrasion of lesions on the walls of hollow organs, in particular blood vessels or the gastrointestinal tract of a patient. The device includes an outer stent which, fixed in position at the site of the lesions, can be clamped against the wall of the hollow organ and has recesses through which the lesions can inwardly protrude. The device further includes a cutting body which is guided within the outer stent and only negligibly narrows the internal bore of the outer stent, which cutting body has cutting edges sliding on the inner side of the outer stent and is coupled magnetically to an external magnet system via which it can turn about the stent axis and/or can move longitudinally along the stent axis.

17 Claims, 1 Drawing Sheet

DEVICE FOR REPEATED SEMI-INVASIVE ABRASION OF LESIONS ON THE WALLS OF HOLLOW ORGANS

The present application hereby claims priority under 35 U.S.C. §119 on German patent application numbers DE 10 2004 009 318.0 filed Feb. 26, 2004, the entire contents of which is hereby incorporated herein by reference.

FIELD OF THE INVENTION

The invention generally relates to a device for repeated semi-invasive abrasion of lesions on the walls of hollow organs, in particular blood vessels or the gastrointestinal tract of a patient.

BACKGROUND OF THE INVENTION

When hollow organs such as blood vessels or the intestine become pathologically altered, for example as a result of growth of malignant or benign tumors or polyps, or as a result of deposits in vessels, the pathological tissue or the deposits are often removed by performing invasive procedures. This is done either surgically or via invasive catheterization. A particular problem in this connection is that the pathological processes are chronic, i.e. the tissue lesions or deposits reappear after just a few weeks or months (a phenomenon called restenosis). Thus, it is necessary to repeat procedures which are expensive and which place a physical burden on the patient. Another factor is that in many cases the areas of the hollow organs to be treated, for example in the small intestine, cannot be reached from outside by catheter.

SUMMARY OF THE INVENTION

It is an object of an embodiment of the invention to make available a device which, without complex catheterization procedures and without surgical interventions, allows semi-invasive abrasion of wall lesions in hollow organs to be performed as often as is necessary.

To achieve an object, such a device includes, according to at least one embodiment of the invention, an outer stent which, fixed in position at the site of the lesions, can be clamped against the wall of the hollow organ and has recesses through which the lesions can inwardly protrude. It further includes a cutting body which is guided within the outer stent and only negligibly narrows the internal bore of the outer stent. The cutting body has cutting edges sliding on the inner side of the outer stent and is coupled magnetically to an external magnet system via which it can turn about the stent axis and/or can move longitudinally along the stent axis.

By such a device according to at least one embodiment of the invention, in which the cutting body can preferably also be a sleeve-shaped inner stent, it is possible, after introducing this device once into the pathologically altered target area of the hollow organ, to simply place the patient within a magnet system and perform repeated abrasion of pathological tissue or of deposits by activating the inner stent and turning it or moving it longitudinally in the outer stent. In a manner known per se, the stents can be tubes of spiral or lattice construction, and the inner stent should have lattice openings with sharp edges so that it can cut off the lesions protruding through the opening of the outer stent.

While the outer stent can be made of high-quality steel or of a biocompatible plastic, the inner stent, because of the need for the sharp edges of the lattice openings, should preferably be made of metal, again of high-quality steel for example.

In order to turn the inner stent in the outer stent via the external magnet system or to move it along the longitudinal axis of the outer stent, the inner stent can either be made at least partially of a magnetic material, or a bar magnet can be secured in the inner stent. In this case, the arrangement and size of the bar magnet is of course chosen such that it takes up only a small part of the cross section, so as to ensure that this bar magnet does not disturb the blood circulation or the normal movement of the intestinal contents.

In a further alternative for moving the inner stent serving as cutting body in the outer stent, it is possible, according to another feature of at least one embodiment of the present invention, for the two stents to be provided, at mutually adjacent ends, with ferromagnetic, preferably annular elements by which they are able to move relative to one another under the effect of an external magnetic field in the direction of the stent axis and counter to the action of a pre-stressing spring. If, for example, the ends provided with the ferromagnetic elements are pressed apart from one another by a pre-stressing spring, or if the remote ends are drawn toward one another by a tension spring, it is possible, by applying an external magnetic field, to effect magnetization of the ferromagnetic elements which then draw toward one another counter to the action of the spring.

When the external magnet system is switched off again, the magnetization ceases, and with it the force of attraction, and the pre-stressing spring shifts the inner stent back into the starting position. When the external magnet system is switched back on, the procedure is repeated. In this way, it is possible to generate a repeated linear cutting cycle by use of a pulsed magnetic excitation.

The outer stent should be provided, at least at one end, preferably at both ends, with inwardly extending limit stops for the inner stent.

A device according to an embodiment of the invention, composed of stents which are movable or rotatable one inside the other, can be introduced with the aid of a catheter, for example.

In cases where such introduction by catheter is not possible, for example in the case already described above where a device according to at least one embodiment of the invention is to be arranged in the small intestine at places which simply cannot be reached from the outside by catheter, the abrasion device according to at least one embodiment of the invention can be introduced, in a further embodiment of the invention, by using an arrangement characterized by a magnet system which covers the treatment area of the patient and which generates a 3D gradient field for remote-controlled movement of an endorobot which is provided with a linear magnet and is freely movable in the hollow organ and to which the stents are coupled and brought to the site of use and there once again uncoupled.

If the external 3D magnetic field can be made strong enough to transport the endorobot with the attached stents to the site of use, counter to the friction of the stents in the hollow organ, the two stents fitted one inside the other should be introduced together in one maneuver.

In most cases, however, such introduction of the opened-out stents cannot be performed with the aid of an endorobot because of the friction in the hollow organ (much greater forces can be applied if they can be introduced with the aid of a catheter). Thus, in this case, first the outer stent is introduced in a folded-down state and is opened out at the site of use, and the inner stent in a folded-down state is then drawn into the already opened-out outer stent and is then opened out.

Provision can be made to ensure that the stent can be folded up resiliently, and the fixing connection can be released from outside when the target site is reached, so that the stent expands radially and optionally also axially and, by bearing against the wall of the hollow organ, is then clamped in place.

Instead of this, provision can also be made for the stent to be made of a shape-memory material, in which case the stent is introduced in the folded state and is heated above the transition temperature in order to open out, so that it then returns to its original form with a larger radial diameter. The heating can be effected by a current pulse which is supplied via the coupling to the endorobot or is fed in inductively from outside.

Finally, the stent may be coated with a medicament, preferably one that dissolves slowly (depot effect), for example with cortisone for long-term treatment of Crohn's disease.

BRIEF DESCRIPTION OF THE DRAWINGS

Further advantages, features and details of the invention will become clear from the following description of an illustrative embodiment given with reference to the drawings, in which.

DETAILED DESCRIPTION OF THE EXEMPLARY EMBODIMENTS

Figure 1:
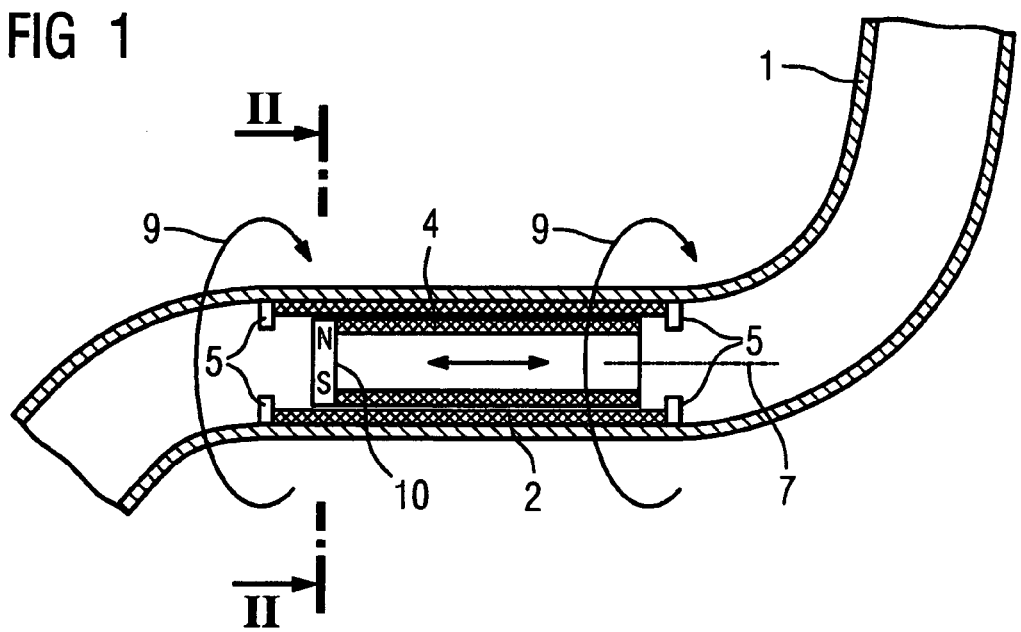
FIG. 1 shows a schematic view of a hollow organ of a patient, for example a blood vessel or the small intestine, with an abrasion device according to the invention made up of two stents which are arranged displaceably one inside the other.
Figure 2:
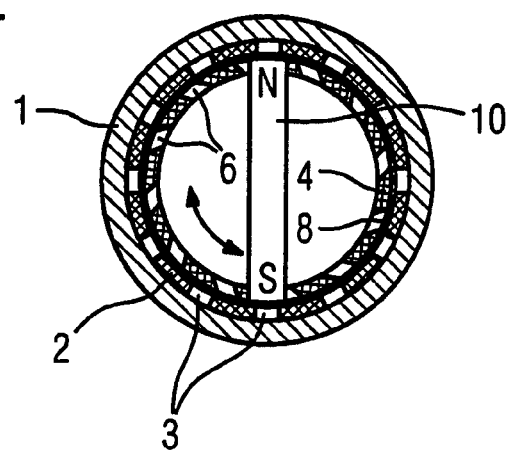
FIG. 2 shows an enlarged cross section along the line II-II in FIG. 1.

The device according to an embodiment of the invention shown in FIGS. 1 and 2 and used for repeated abrasion of lesions on the walls of a hollow organ 1, for example a blood vessel or the small intestine, is made up of an outer stent 2 in the form of a tube of spiral or lattice construction, through whose openings 3 the pathological tissue or the deposits can grow or be pressed inward. Mounted so as to be able to slide inside this outer stent 2 there is an inner stent 4 which can likewise be designed as a tube of spiral or lattice construction, and inwardly extending limit stops 5 at the ends of the outer stent prevent escape of the inner stent from the outer stent.

The inner stent has lattice openings 6 with sharp edges, so that, upon movement of the inner stent 4, whether this be a rotation movement about the longitudinal axis 7 of the stent or a linear movement along the longitudinal axis 7 of the stent, the lesions which are to be removed and which protrude into the inside of the outer stent can be cut off cleanly by these sharp edges 8. The inner stent is moved using an external magnet system (not shown) which, in the illustrative embodiment according to FIGS. 1 and 2, is a rotating field indicated by the magnet arrows 9, by which the inner stent, provided with a transversely built-in bar magnet 10, is able to turn about the axis 7.

Instead of providing a built-in bar magnet 10, it could also be possible to provide transverse magnetization of the inner stent 4, which accordingly is made at least partially of magnetic material.

Figure 3:
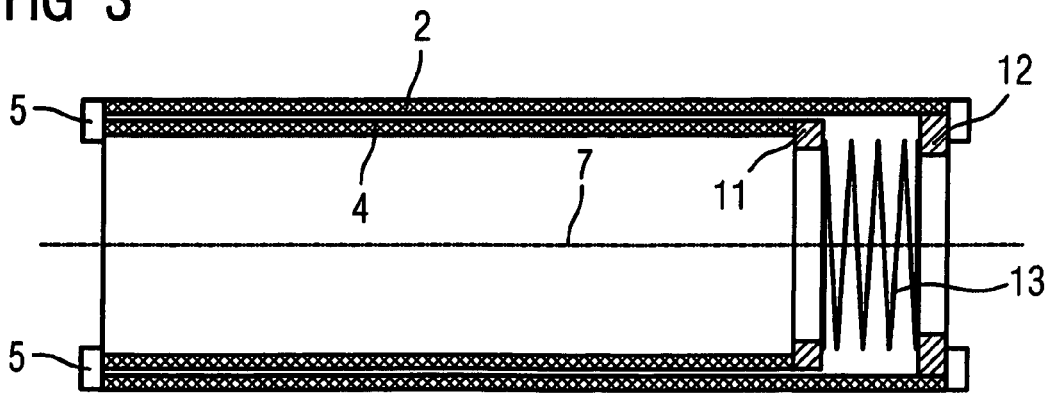
FIG. 3 shows a modified embodiment of a device according to the invention in which the stents arranged one inside the other can be moved by ferromagnetic rings in the external magnetic field.

FIG. 3 shows a modified illustrative embodiment in which the inner stent 4 and the outer stent 2 are provided, at mutually adjacent ends, with ferromagnetic rings 11 and 12 and these two ends are pressed apart from one another by a pressure spring 13. By applying an external magnetic field parallel to the longitudinal axis 7 of the stents, the ferromagnetic rings 11 and 12 are magnetized and accordingly attracted to each other and thus move the inner stent 4 to the right in the outer stent 2 counter to the action of the pre-stressing spring 13. When the external magnetic field is switched off, the spring 13 presses the inner stent back toward the left, so that an oscillating cutting movement can be achieved through a pulsed external linear magnetic field.

The manner of inserting stents with the aid of a catheter is sufficiently well known, as is also the introduction of stents using an endorobot, as described in German Patent DE 101 42 253 C1, the entire contents of which are hereby incorporated herein by reference. There is therefore no need at this point to go into detail concerning this possible introduction of the stents. Introduction of the stents in the folded-up state is described in detail in a parallel patent application.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for repeated semi-invasive abrasion of lesions on walls of a hollow organ, comprising:
    an outer stent having recesses through which the lesions can inwardly protrude, wherein the outer stent is configured to clamp against the walls of the hollow organ at a site of the lesions; and
    a magnetically-controllable cutting body guided within the outer stent and only negligibly narrowing an internal bore of said outer stent, the cutting body including cutting edges sliding on an inner side of the outer stent and being coupled magnetically to an external magnet system via which the cutting body is configured to turn about a stent axis in order to perform abrasion,
    the cutting body being a sleeve-shaped inner stent, wherein the inner stent is made at least partially of a magnetic material and is magnetized in a traverse direction of the stent axis, and
    the inner stent being completely mounted inside the outer stent so as to slide inside the outer stent so that upon movement of the inner stent lesions protruding into the inside of the outer stent can be cut off, whereby the outer stent includes at least one inwardly-extending limit stop preventing escape of the inner stent from the outer stent.

2. The device as claimed in claim 1, wherein the stents are tubes of spiral or lattice construction.

3. The device as claimed in claim 2, wherein the inner stent includes lattice openings with sharp edges.

4. The device as claimed in claim 1, wherein the outer stent is made of a high-quality steel or a biocompatible plastic, and the inner stent is made of a metal.

5. The device as claimed in claim 1, wherein the two stents have, at mutually adjacent ends, ferromagnetic elements for movement relative to one another under effects of an external magnetic field in a direction of the stent axis and counter to movement of a pre-stressing spring.

6. The device as claimed in 1, wherein the device is for repeated semi-invasive abrasion of the lesions on the walls of at least one of blood vessels and a gastrointestinal tract of a patient.

7. An arrangement for introducing a device, for semi-invasive abrasion of lesions on walls of a hollow organ, into the hollow organ of a patient, the arrangement comprising:
    a magnet system that covers a treatment area of the patient and generates a 3D gradient field for remote-controlled movement of an endorobot provided with a linear magnet and freely movable in the hollow organ, wherein the device is positioned at a site of use by coupling the device to the endorobot, bringing the endorobot to the site of use and uncoupling the device from the endorobot, the device including, an outer stent having recesses through which the lesions can inwardly protrude, wherein the outer stent is configured to clamp against the walls of the hollow organ at a site of the lesions; and a magnetically-controllable cutting body guided within the outer stent and only negligibly narrowing an internal bore of said outer stent, the cutting body including cutting edges sliding on an inner side of the outer stent and being coupled magnetically to the magnet system via which the cutting body is configured to turn about a stent axis in order to perform abrasion, the cutting body being a sleeve-shaped inner stent, wherein the inner stent is made at least partially of a magnetic material and is magnetized in a traverse direction of the stent axis, and the inner stent being completely mounted inside the outer stent so as to slide inside the outer stent so that upon movement of the inner stent lesions protruding into the inside of the outer stent can be cut off, whereby the outer stent includes at least one inwardly-extending limit stop preventing escape of the inner stent from the outer stent.

8. The arrangement as claimed in claim 7, wherein the two stents fitted one inside the other are introduced together.

9. The arrangement as claimed in claim 7, wherein the outer stent is introduced in a folded-down state and opened out at the site of use, and the inner stent in the folded-down state is subsequently drawn into the opened-out outer stent and opened out.

10. The arrangement as claimed in claim 9, wherein at least one of the stents folds up resiliently, and a fixing connection is released from outside such that the at least one of stent expands radially by bearing against the wall of the hollow organ.

11. The arrangement as claimed in claim 9, wherein at least one of the stents is made of a shape-memory material and heated above a transition temperature in order to open out.

12. The arrangement as claimed in claim 11, wherein the heating is effected by a current pulse which is supplied via the coupling to the endorobot and fed in inductively from outside.

13. The arrangement as claimed in claim 7, wherein at least one of the stents is made of, or coated with, a biocompatible material.

14. The arrangement as claimed in claim 7, wherein at least one of the stents is coated with a medicament.

15. The arrangement as claimed in claim 14, wherein the medicament is one that dissolves.

16. A device for repeated semi-invasive abrasion of lesions on walls of a hollow organ, comprising:

an outer stent having recesses through which the lesions can inwardly protrude, wherein the outer stent is configured to clamp against the walls of the hollow organ at a site of the lesions; and a magnetically-controllable cutting body guided within the outer stent and only negligibly narrowing an internal bore of said outer stent, the cutting body including cutting edges sliding on an inner side of the outer stent and being coupled magnetically to an external magnet system via which the cutting body is configured to turn about a stent axis in order to perform abrasion, the cutting body being a sleeve-shaped inner stent, wherein a bar magnet is secured in the inner stent, and the inner stent being completely mounted inside the outer stent so as to slide inside the outer stent so that upon movement of the inner stent lesions protruding into the inside of the outer stent can be cut off, whereby the outer stent includes two inwardly-extending limit stops, delimiting opposing ends of the inner outer stent, preventing escape of the inner stent from the outer stent.

17. The device as claimed in claim 16, wherein the bar magnet extends across a cross-sectional area of the inner stent.

* * * * *